United States Patent
Heeren

(10) Patent No.: US 10,460,457 B2
(45) Date of Patent: Oct. 29, 2019

(54) ADAPTIVE ADJUSTMENT OF OVERLAY IMAGE PARAMETERS

(71) Applicant: Novartis AG, Basel (CH)

(72) Inventor: Tammo Heeren, Aliso Viejo, CA (US)

(73) Assignee: Novartis AG (CH)

( * ) Notice: Subject to any disclaimer, the term of this patent is extended or adjusted under 35 U.S.C. 154(b) by 53 days.

(21) Appl. No.: 15/621,069

(22) Filed: Jun. 13, 2017

(65) Prior Publication Data

US 2018/0018780 A1 Jan. 18, 2018

Related U.S. Application Data

(60) Provisional application No. 62/361,357, filed on Jul. 12, 2016.

(51) Int. Cl.
| | |
|---|---|
| *G06T 7/30* | (2017.01) |
| *G06T 11/60* | (2006.01) |
| *G06T 7/00* | (2017.01) |
| *A61F 9/007* | (2006.01) |
| *A61B 3/00* | (2006.01) |
| *A61B 3/13* | (2006.01) |
| *G06T 11/00* | (2006.01) |

(52) U.S. Cl.
CPC .............. *G06T 7/30* (2017.01); *A61B 3/0025* (2013.01); *A61B 3/13* (2013.01); *A61F 9/007* (2013.01); *G06T 7/0014* (2013.01); *G06T 11/00* (2013.01); *G06T 11/60* (2013.01); *G06T 2207/10056* (2013.01); *G06T 2207/30041* (2013.01)

(58) Field of Classification Search
None
See application file for complete search history.

(56) References Cited

U.S. PATENT DOCUMENTS

| | | | | |
|---|---|---|---|---|
| 8,432,414 B2* | 4/2013 | Vetterli | ............... | G01C 21/20 |
| | | | | 345/632 |
| 2009/0054908 A1* | 2/2009 | Zand | ............... | A61B 5/0071 |
| | | | | 606/130 |
| 2015/0173644 A1* | 6/2015 | Ren | ............... | A61B 5/066 |
| | | | | 600/424 |
| 2015/0289945 A1* | 10/2015 | Nguyen | ............... | A61F 2/02 |
| | | | | 623/23.72 |
| 2016/0183779 A1* | 6/2016 | Ren | ............... | A61B 3/0058 |
| | | | | 351/206 |
| 2017/0082847 A1* | 3/2017 | Wilzbach | ............ | G02B 21/0012 |
| 2018/0018780 A1* | 1/2018 | Heeren | ............... | G06T 7/30 |

* cited by examiner

*Primary Examiner* — Tahmina N Ansari

(74) *Attorney, Agent, or Firm* — Keiko Ichiye, Esq.

(57) ABSTRACT

Image parameters of an overlay image may be adjusted based on image parameters of an optical image displayed in a surgical microscope. The overlay image may then be displayed with the optical image to a user of the surgical microscope.

14 Claims, 5 Drawing Sheets

ADAPTIVE ADJUSTMENT OF OVERLAY IMAGE PARAMETERS

BACKGROUND

Field of the Disclosure

The present disclosure relates to ophthalmic surgery, and more specifically, to adaptive adjustment of overlay image parameters.

Description of the Related Art

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging of the fundus during vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus.

In addition to viewing the fundus, some surgical microscopes may be equipped with optical scanners to provide additional information about portions of eye tissue involved with the vitreoretinal surgery. The optical scanners may be optically or electro-mechanically integrated into the surgical microscope. One type of commonly used optical scanner in ophthalmology is optical coherence tomography (OCT), which is also used during vitreoretinal surgery and may be integrated with the optics of a surgical microscope. The output images from optical scanners may be overlaid onto the surgical microscopy display image for simultaneous viewing by a user.

SUMMARY

The disclosed embodiments of the present disclosure provide a method and system to adaptively adjust overlay image parameters for improved viewing by the user during ophthalmic surgery. The methods and systems disclosed herein for adaptive adjustment of overlay image parameters may be used during vitreoretinal surgery and may be integrated to output an overlay image that is viewed via an ocular of a surgical microscope or an external display. The methods and systems disclosed herein for adaptive adjustment of overlay image parameters may be used in conjunction with diagnostic or clinical procedures that involve viewing the fundus, and in particular, the macula. The methods and systems disclosed herein for adaptive adjustment of overlay image parameters may improve the quality of overlay images displayed to the user, without relying on user input for overlay image adjustment.

In one aspect, a disclosed method is for image processing. The method includes receiving an overlay image for display with an optical image generated by a surgical microscope, and scanning the optical image to generate optical image parameters. Based on the optical image parameters, the method also includes generating overlay image parameters to correspond to the optical image parameters, applying the overlay image parameters to the overlay image, and displaying the overlay image having the overlay image parameters with the optical image.

In any of the disclosed embodiments of the method, displaying the overlay image may further include overlaying the overlay image onto a portion of the optical image.

In any of the disclosed embodiments of the method, the overlay image may include transparent portions, while displaying the overlay image may further include overlaying the overlay image onto the optical image, such that the overlay image and the optical image are the same size.

In any of the disclosed embodiments of the method, the optical image parameters and the overlay image parameters may include at least one of brightness, contrast, and color scale.

In any of the disclosed embodiments of the method, the overlay image may include optical scan data from an optical scanner.

In any of the disclosed embodiments of the method, displaying the overlay image may further include outputting the overlay image to an ocular of the surgical microscope.

In any of the disclosed embodiments of the method, generating the overlay image parameters to correspond to the optical image parameters may further include matching the overlay image parameters to the optical image parameters.

Another disclosed aspect includes an image processing system for adaptive adjustment of overlay image parameters, the image processing system including a processor enable to access memory media storing instructions executable by the processor to perform the method. A further disclosed aspect includes an article of manufacture comprising non-transitory memory media for adaptive adjustment of overlay image parameters, the memory media storing instructions executable by a processor to perform the method.

BRIEF DESCRIPTION OF THE DRAWINGS

For a more complete understanding of the present invention and its features and advantages, reference is now made to the following description, taken in conjunction with the accompanying drawings, in which.

DESCRIPTION OF PARTICULAR EMBODIMENT(S)

Figure 1:
FIG. 1 shows an embodiment of a surgical microscopy display image with an overlay image.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, during vitreoretinal surgery a surgeon may view the fundus of an eye of a patient using a surgical microscope, for example, in conjunction with a contact lens placed on the cornea. The surgeon may then view optical images of the operation using the surgical microscope.

Optical coherence tomography (OCT) is a noninvasive cross-sectional imaging technique that is widely used in diagnostic and clinical ophthalmology. Although OCT scanners have been integrated with the optics of surgical microscopes, user operation of the resulting instrumentation may be unwieldy and impractical for use during vitreoretinal surgery. In particular, the surgeon may desire to spatially correlate the location of the optical scan, as well as scan data indicative of the profile depth scan, with the optical image from the surgical microscope, which may be difficult or time-consuming to perform during vitreoretinal surgery using different systems (i.e., the surgical microscope and the optical scanner) with independent operation and display outputs. Furthermore, when the scanning images are overlaid as overlay images onto the optical image from the surgical microscope, differences in image quality between the two images may be an impediment by reducing the ability of the human eye to see certain details. For example, when the brightness between the two images exhibits a large difference, the less bright image may be difficult to see for the user. Other differences in contrast as well as color palette may also be similarly disadvantageous during ophthalmic surgery when viewing overlay images with the optical images.

The present disclosure relates to adaptive adjustment of overlay image parameters. As will be described in further detail, when an overlay image is to be displayed with an optical image in a surgical microscope, certain image parameters of the optical image may be generated. For example, the optical image may be scanned (or digitized) to generate the image parameters, such as brightness, contrast, and color palette. Then, the image parameters of the overlay image may be modified to correspond to the image parameters of the optical image. In this manner, the overlay image may be displayed with an improved image quality and improved viewability to the user, absent any user input or user actions to adjust the image parameters, which is desirable in a surgical environment.

Referring now to the drawings, FIG. 1 shows an embodiment of a surgical microscopy display image 100. Surgical microscopy display image 100 may represent an image viewed through the ocular of a surgical microscope during ophthalmic surgery. As shown, surgical microscopy display image 100 includes overlay image 102 and optical image 104, which may be the same size. Overlay image 102 may include certain transparent portions and may display certain regions of interest, such as locations associated with a membrane, as masked regions. Optical image 104 may represent the image generated by the surgical microscope.

The image parameters of overlay image 102 may be selected to match certain image parameters of optical image 104, such as contrast or brightness, in order to maintain overall viewability of surgical microscopy display image 100. Meanwhile, certain other image parameters of overlay image 102 may be chosen to contrast with optical image 104, such as color palette (defined as a color scale for a range of pixel values), in particular embodiments, for example, to enable overlay image to be distinguished, as desired.

Figure 2:
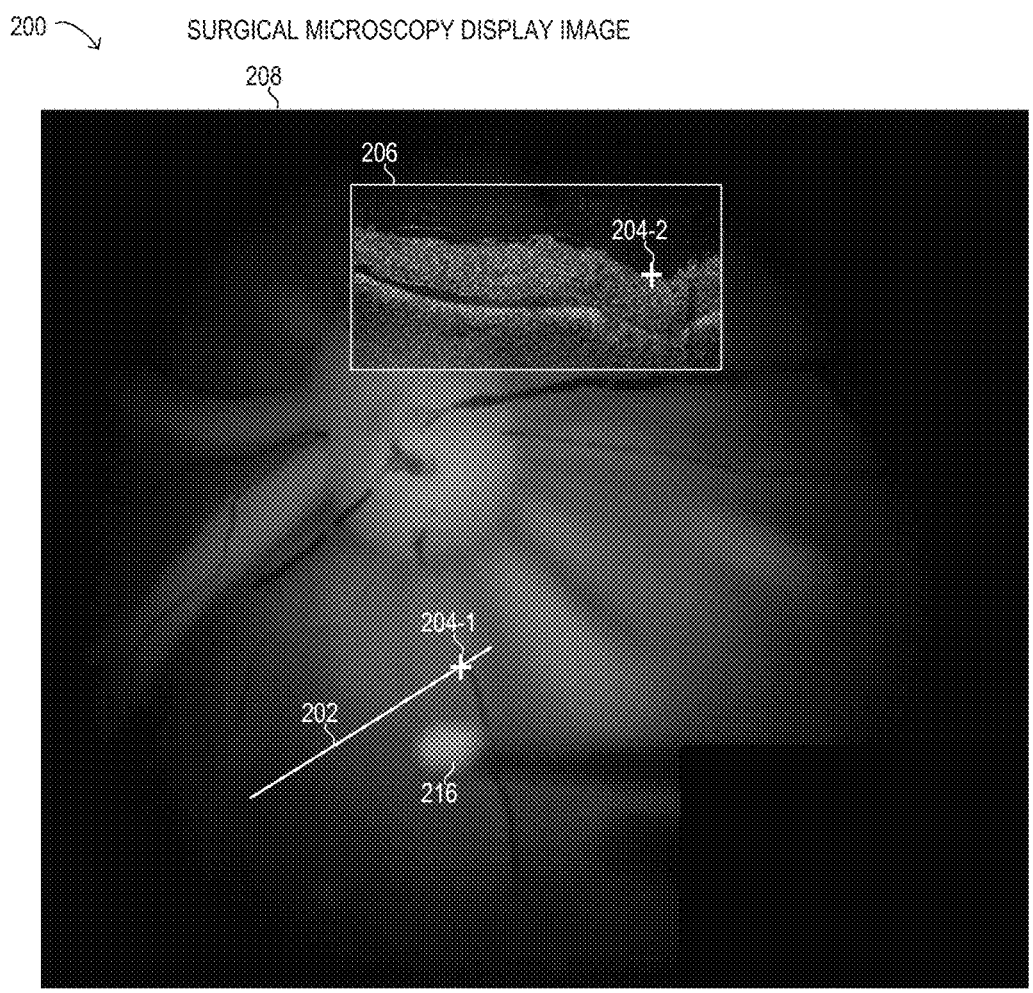
FIG. 2 shows an embodiment of a surgical microscopy display image with an overlay image.

FIG. 2 shows an embodiment of a surgical microscopy display image 200. Display image 200 may represent a field of view seen by the user operating a surgical microscope that is integrated with an OCT scanner (see FIG. 5). As shown, surgical microscopy display image 200 includes optical image 208 that is generated by the surgical microscope. Optical image 208 may include a view of the fundus of the eye, and may show certain surgical tools or instruments. In FIG. 2, an illuminator 216 is visible in the fundus in optical image 208. In addition to optical image 208, surgical microscopy display image 200 includes an overlay image 206 that is overlaid onto optical image 208.

Specifically, in FIG. 2, a display element 202 is indicative of the selected portion at a location in the fundus where a line scan for optical scanning has been chosen by the user. Additionally, overlay image 206 shows scan data in the form of a 2D depth profile image corresponding to display element 202. Furthermore, marker 204 also shows a specific location that the user can select. Marker 204 may be limited to a position along the line scan specified by display element 202. Marker 204-1 shows the marked location on display element 202, while marker 204-2 shows the corresponding marked location on overlay image 206. Although a 2D line scan is shown in FIG. 2 for descriptive clarity, it will be understood that display element display element 202 may be a 2D area, while overlay image 206 depicts 3D scan data.

As noted, when the image parameters of overlay image 206 do not correspond (or match) certain image parameters of optical image 208, the overall image quality for the user may be reduced, which is undesirable. FIG. 2 is an example of using overlay image 206 on top of optical image 208, such that the image parameters may also include a location of overlay image 206 relative to optical image 208. It is noted that while a 2D line scan image is shown displayed in overlay image 206, various different kinds of images or scan results may be displayed in overlay image 206.

The image parameters of overlay image 206 may be selected to match certain image parameters of optical image 208, such as contrast or brightness, in order to maintain overall viewability of surgical microscopy display image 200. Meanwhile, certain other image parameters of overlay image 206 may be chosen to contrast with optical image 208, such as color palette (defined as a color scale for a range of pixel values), in particular embodiments, for example, to enable overlay image to be distinguished, as desired. In some embodiments, the color palette of overlay image 206 may be chosen to correspond to the color palette of optical image 208.

Figure 3:
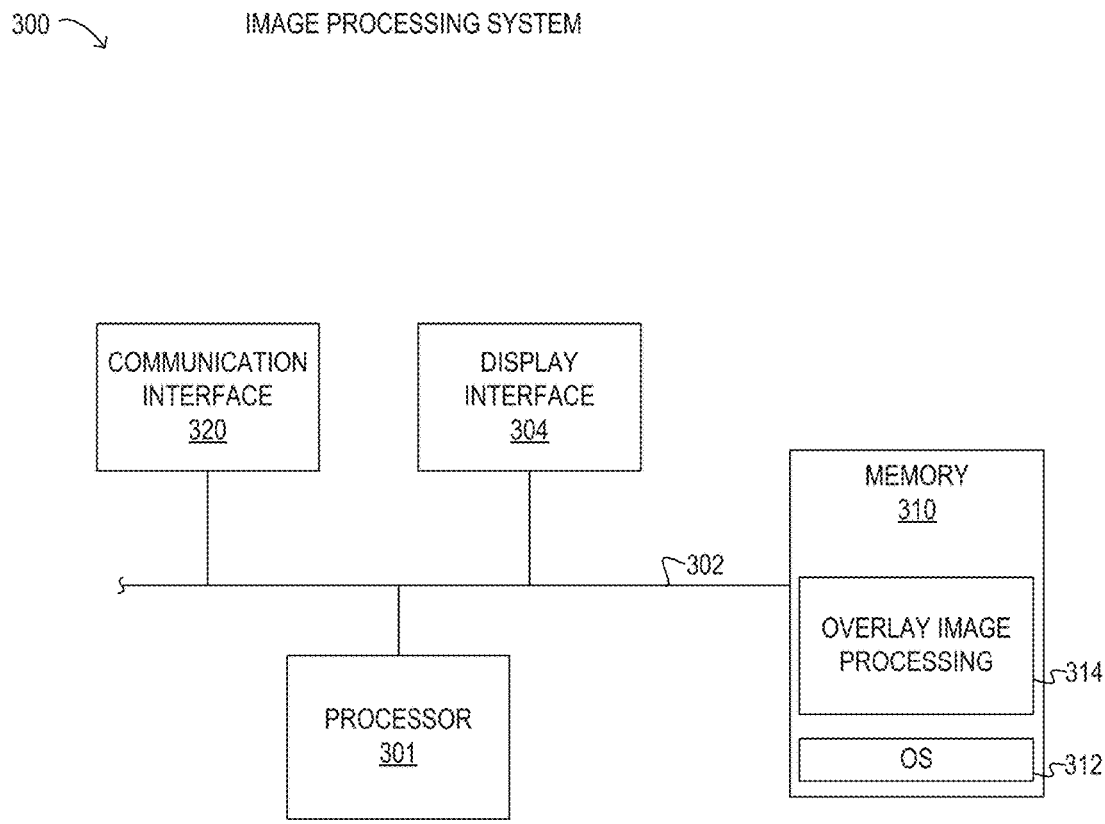
FIG. 3 is a block diagram of selected elements of an embodiment of an image processing system.

Referring now to FIG. 3, a block diagram illustrating selected elements of an embodiment of an image processing system 300 is presented. In the embodiment depicted in FIG.

3, image processing system 300 includes processor 301 coupled via shared bus 302 to memory media collectively identified as memory 310.

Image processing system 300, as depicted in FIG. 3, further includes communication interface 320 that can interface image processing system 300 to various external entities, such as an OCT scanner (not shown) to receive 2D line scan data or 3D scan data. In some embodiments, communication interface 320 is operable to enable image processing system 300 to connect to a network (not shown in FIG. 3). In embodiments suitable for adaptive adjustment of overlay image parameters, image processing system 300, as depicted in FIG. 3, includes display interface 304 that connects shared bus 302, or another bus, with an output port for one or more displays, such as an ocular display of a surgical microscope or a display outside a surgical microscope.

In FIG. 3, memory 310 encompasses persistent and volatile media, fixed and removable media, and magnetic and semiconductor media. Memory 310 is operable to store instructions, data, or both. Memory 310 as shown includes sets or sequences of instructions, namely, an operating system 312, and an overlay image processing application 314. Operating system (OS) 312 may be a UNIX or UNIX-like operating system, a Windows® family operating system, or another suitable operating system.

In various embodiments, image processing system 300 may be integrated with different types of equipment. In one embodiment, image processing system 300 is integrated with a surgical microscope. In given embodiments, image processing system 300 may directly interface with an OCT scanner. In some embodiments, image processing system 300 is a standalone system that receives OCT scan data and optical image data, and then outputs overlay image data, as described herein.

Figure 4:
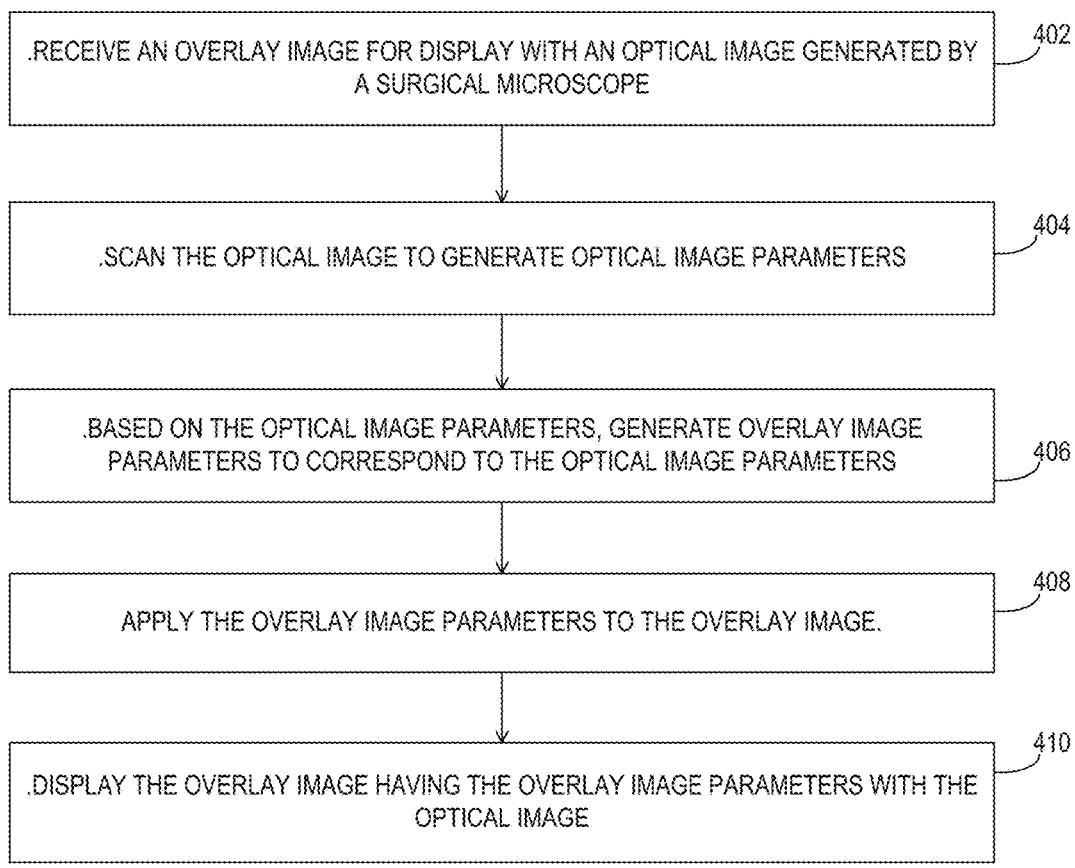
FIG. 4 is a flow chart of selected elements of a method for adaptive adjustment of overlay image parameters.

Referring now to FIG. 4, a flow chart of selected elements of an embodiment of a method 400 for characterizing membranes at vitreoretinal interfaces, as described herein, is depicted in flowchart form. It is noted that certain operations described in method 400 may be optional or may be rearranged in different embodiments. Method 400 may be performed by membrane image processing application 314 in FIG. 3. It is noted that method 400 may be repeated in an ongoing manner, such as during ophthalmic surgery, for example, to continuously adapt to changes in the optical image viewed using the surgical microscope.

Method 400 may begin, at step 402, by receiving an overlay image for display with an optical image generated by a surgical microscope. At step 404, the optical image is scanned to generate optical image parameters. The image parameters may include brightness, contrast, and color palette. At step 406, based on the optical image parameters, overlay image parameters are generated to correspond to the optical image parameters. At step 408, the overlay image parameters are applied to the overlay image. At step 410, the overlay image having the overlay image parameters are displayed with the optical image.

Figure 5:
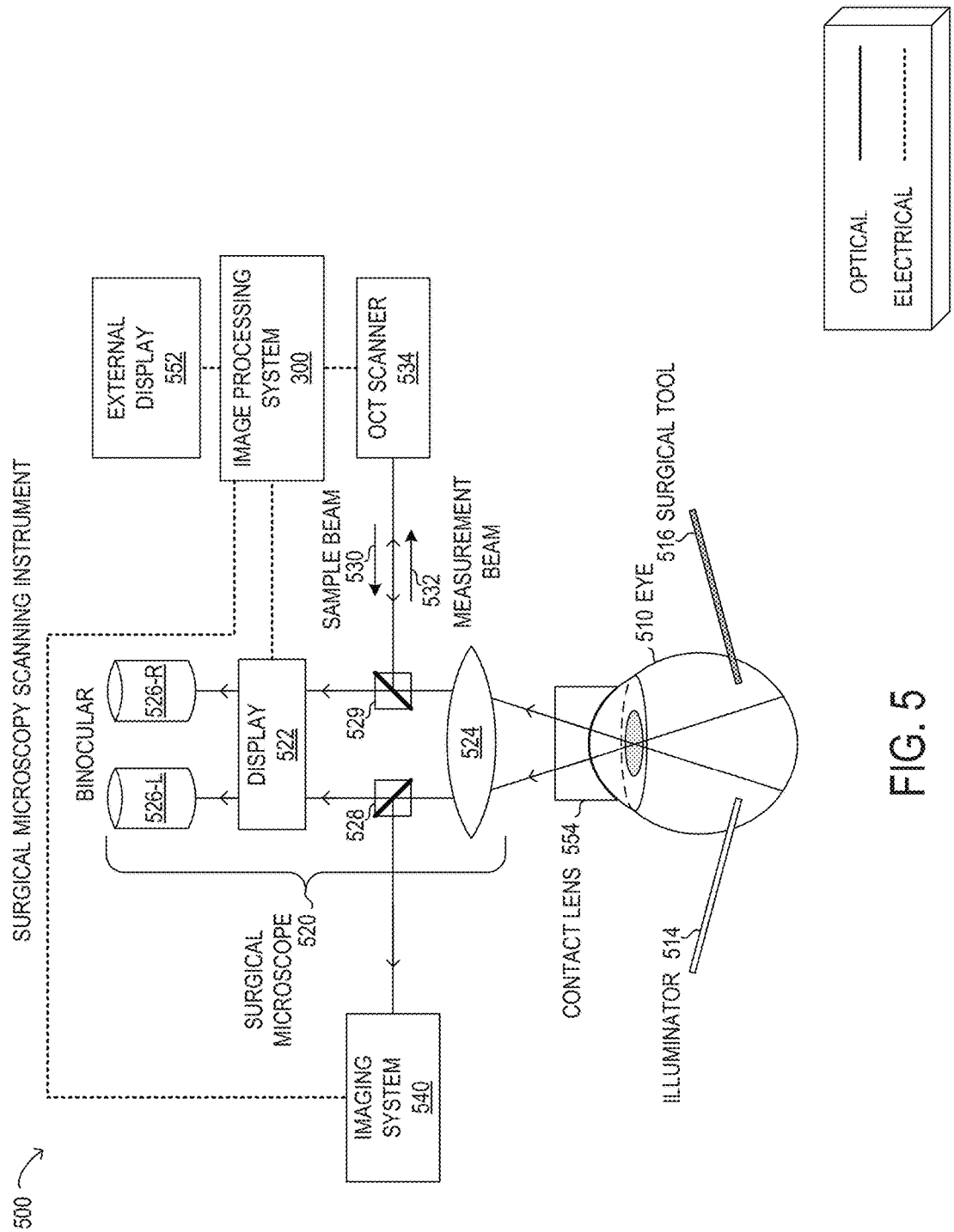
FIG. 5 is a block diagram of selected elements of an embodiment of a surgical microscopy scanning instrument.

FIG. 5 is a block diagram showing a surgical microscopy scanning instrument 500. Instrument 500 is not drawn to scale but is a schematic representation. Instrument 500 may be used during vitreoretinal surgery to view and analyze a human eye 510. As shown, instrument 500 includes surgical microscope 520, image processing system 300, external display 552, and OCT scanner 534. Also shown in FIG. 5 are imaging system 540, contact lens 554, as well as surgical tool 516 and illuminator 514.

As shown, surgical microscope 520 is depicted in schematic form to illustrate optical functionality. It will be understood that surgical microscope 520 may include various other electronic and mechanical components, in different embodiments. Accordingly, objective 524 may represent a selectable objective to provide a desired magnification or field of view of the fundus. Objective 524 may receive light from the fundus of eye 510 via contact lens 554 that rests on a cornea of eye 510. It is noted that other types of lenses at eye 510 may be used with surgical microscope 520. To perform vitreoretinal surgery, various tools and instruments may be used, including tools that penetrate the sclera, represented by surgical tool 516. Illuminator 514 may be a special tool that provides a light source from within the fundus of eye 510.

In FIG. 5, surgical microscope 520 is shown with a binocular arrangement with two distinct but substantially equal light paths that enable viewing with binoculars 526 that comprise a left ocular 526-L and a right ocular 526-R. From objective 524, a left light beam may be split at beam splitter 528, from where imaging system 540 and left ocular 526-L receive the optical image. Also from objective 524, a right light beam may be split at partial mirror 529, which also receives sample beam 530 from OCT scanner 534, and outputs measurement beam 532 to OCT scanner 534. Partial mirror 529 also directs a portion of the right light beam to right ocular 526-R. Display 522 may represent an optoelectronic component, such as an image processing system that receives data from image processing system 300 and generates overlay image 201 for left ocular 526-L and right ocular 526-R, respectively. In some embodiments, display 522 includes miniature display devices that output images to binoculars 526 for viewing by the user.

In FIG. 5, image processing system 300 may have an electrical interface with display 522, for example, for outputting display data. In this manner, image processing system 300 may receive optical image data from imaging system 540, may modify the optical image data as described herein, and may output a display image to display 522 that is viewed at binoculars 526. The display image output to display 522 or external display 552 by image processing system 300 may correspond to overlay image 201, as described previously. Because the electrical interface between display 522 and image processing system 300 may support digital image data, image processing system 300 may perform image processing in real-time with relatively high frame refresh rates. External display 552 may output similar images as display 522, but may represent a standalone monitor for viewing by various personnel during vitreoretinal surgery. Display 522 or external display 552 may be implemented as a liquid crystal display screen, a computer monitor, a television or the like. Display 522 or external display 552 may comply with a display standard for the corresponding type of display, such as video graphics array (VGA), extended graphics array (XGA), digital visual interface (DVI), high-definition multimedia interface (HDMI), etc.

With the binocular arrangement of surgical microscope 520 in FIG. 5, imaging system 540 may receive a portion of the left light beam that enables imaging system 540 to independently process, display, store, and otherwise manipulate light beams and image data. Accordingly, imaging system 540 may represent any of a variety of different kinds of imaging systems, as desired.

As shown, OCT scanner 534 may represent an embodiment of an optical scanner. It is noted that other types of optical scanners may be used with the arrangement depicted in FIG. 5. OCT scanner 534 may control output of sample beam 530 and may receive measurement beam 532 that is reflected back in response to photons of sample beam 530 interacting with tissue in eye 510. OCT scanner 534 may also be enabled to move sample beam 530 to the selected location indicated by the user. Image processing system 300 may interface with OCT scanner 534, for example, to send commands to OCT scanner 534 indicating the selected location to generate scan data, and to receive the scan data from OCT scanner 534. It is noted that OCT scanner 534 may represent various types of OCT instruments and configurations, as desired, such as but not limited to time domain OCT (TD-OCT) and frequency domain OCT (FD-OCT). In particular, the scan data generated by OCT scanner 534 may include two-dimensional (2D) scan data of a line scan and three-dimensional (3D) scan data for an area scan. The scan data may represent a depth profile of the scanned tissue that enables imaging below a visible surface within the fundus of eye 510, such as shown in OCT line scan data 100 (see FIG. 1).

In operation of instrument 500, the user may view an optical image of the fundus of eye 510 using binoculars while vitreoretinal surgery is performed on eye 510. The user may provide user input to operate OCT scanner 534. For example, the user input may include a first indication of a selected location within the field of view for generating scan data. Image processing system 300 may then receive the scan data from OCT scanner 534 and generate an overlay image from the scan data. The overlay image may then be adaptively adjusted, as described herein, such that image parameters of the overlay image correspond to image parameters of the optical image.

Modifications, additions, or omissions may be made to surgical microscopy scanning instrument 500 without departing from the scope of the disclosure. The components and elements of surgical microscopy scanning instrument 500, as described herein, may be integrated or separated according to particular applications. Surgical microscopy scanning instrument 500 may be implemented using more, fewer, or different components in some embodiments.

As disclosed herein, image parameters of an overlay image may be adjusted based on image parameters of an optical image displayed in a surgical microscope. The overlay image may then be displayed with the optical image to a user of the surgical microscope.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for image processing, the method comprising:
    displaying an optical image of an eye generated by a surgical microscope;
    receiving a location of the eye selected by a user using the optical image;
    scanning the location of the eye to generate an OCT overlay image showing a depth profile of the location;
    generating optical image parameters from the optical image, the optical image parameters including at least one of: a brightness, a contrast, and a color scale;
    based on the optical image parameters, generating OCT overlay image parameters to match the optical image parameters;
    applying the OCT overlay image parameters to the OCT overlay image of the depth profile of the location; and
    displaying on a display the OCT overlay image of the depth profile with the optical image, the OCT overlay image having the overlay image parameters that match the optical image parameters.

2. The method of claim 1, wherein displaying the overlay image further comprises:
    overlaying the overlay image onto a portion of the optical image.

3. The method of claim 1, wherein the overlay image includes transparent portions, and wherein displaying the overlay image further comprises:
    overlaying the overlay image onto the optical image, wherein the overlay image and the optical image are the same size.

4. The method of claim 1, wherein the overlay image includes optical scan data from an optical scanner.

5. The method of claim 1, wherein displaying the overlay image further comprises:
    outputting the overlay image to an ocular of the surgical microscope.

6. An image processing system comprising:
    a processor enable to access memory media storing instructions executable by the processor to:
        display an optical image of an eye generated by a surgical microscope;
        receive a location of the eye selected by a user using the optical image;
        scan the location of the eye to generate an OCT overlay image showing a depth profile of the location;
        generate optical image parameters from the optical image, the optical image parameters including at least one of: a brightness, a contrast, and a color scale;
        based on the optical image parameters, generate OCT overlay image parameters to match the optical image parameters; and
        apply the OCT overlay image parameters to the OCT overlay image of the depth profile of the location; and
    a display configured to display the OCT overlay image of the depth profile with the optical image, the OCT overlay image having the overlay image parameters that match the optical image parameters.

7. The image processing system of claim 6, wherein the instructions to display the overlay image further comprise instructions to:
    overlay the overlay image onto a portion of the optical image.

8. The image processing system of claim 6, wherein the overlay image includes transparent portions, and wherein the instructions to display the overlay image further comprise instructions to:
    overlay the overlay image onto the optical image, wherein the overlay image and the optical image are the same size.

9. The image processing system of claim 6, wherein the overlay image includes optical scan data from an optical scanner.

10. The image processing system of claim 6, wherein the instructions to display the overlay image further comprise instructions to:
    output the overlay image to an ocular of the surgical microscope.

11. An article of manufacture comprising non-transitory memory media for image processing, the memory media storing instructions executable by a processor to:
    display an optical image of an eye generated by a surgical microscope;

receive a location of the eye selected by a user using the optical image;
scan the location of the eye to generate an OCT overlay image showing a depth profile of the location;
generate optical image parameters from the optical image, the optical image parameters including at least one of: a brightness, a contrast, and a color scale;
based on the optical image parameters, generate OCT overlay image parameters to match the optical image parameters;
apply the OCT overlay image parameters to the OCT overlay image of the depth profile of the location; and
display on a display the OCT overlay image of the depth profile with the optical image, the OCT overlay image having the overlay image parameters that match the optical image parameters.

12. The article of manufacture of claim 11, wherein the instructions to display the overlay image further comprise instructions to:
overlay the overlay image onto a portion of the optical image.

13. The article of manufacture of claim 11, wherein the overlay image includes transparent portions, and wherein the instructions to display the overlay image further comprise instructions to:
overlay the overlay image onto the optical image, wherein the overlay image and the optical image are the same size.

14. The article of manufacture of claim 11, wherein the overlay image includes optical scan data from an optical scanner, and wherein the instructions to display the overlay image further comprise instructions to:
output the overlay image to an ocular of the surgical microscope.

* * * * *